(12) United States Patent  (10) Patent No.: US 6,689,140 B2
Cohen  (45) Date of Patent: Feb. 10, 2004

(54) SYSTEM AND METHOD FOR SPINAL RECONSTRUCTION

(75) Inventor: Herb Cohen, Shelton, CT (US)

(73) Assignee: Howmedica Osteonics Corp., Allendale, NJ (US)

( * ) Notice: Subject to any disclaimer, the term of this patent is extended or adjusted under 35 U.S.C. 154(b) by 0 days.

(21) Appl. No.: 09/968,694

(22) Filed: Oct. 1, 2001

(65) Prior Publication Data

US 2002/0072753 A1 Jun. 13, 2002

Related U.S. Application Data

(60) Provisional application No. 60/237,169, filed on Oct. 2, 2000.

(51) Int. Cl.[7] .............................................. A61B 17/58
(52) U.S. Cl. ......................... 606/103; 606/139; 606/148
(58) Field of Search ................................. 606/102, 103, 606/232, 139, 148

(56) References Cited

U.S. PATENT DOCUMENTS

| 4,570,618 A | 2/1986 | Wu |
| 4,790,303 A | 12/1988 | Steffee |
| 4,966,600 A | 10/1990 | Songer et al. |
| 5,057,113 A | 10/1991 | Mingozzi |
| 5,092,868 A | 3/1992 | Mehdian |
| 5,116,340 A | 5/1992 | Songer et al. |
| 5,123,910 A | 6/1992 | McIntosh |
| 5,304,178 A | 4/1994 | Stahurski |
| 5,312,410 A | 5/1994 | Miller et al. |
| 5,352,225 A | 10/1994 | Yuan et al. |
| 5,395,374 A | 3/1995 | Miller et al. |
| 5,417,690 A | 5/1995 | Sennett et al. |
| 5,431,659 A | 7/1995 | Ross, Jr. et al. |
| 5,449,361 A | 9/1995 | Preissman |
| 5,476,465 A | 12/1995 | Preissman |
| 5,496,318 A | 3/1996 | Howland et al. |
| 5,536,270 A | 7/1996 | Songer et al. |
| 5,540,698 A | 7/1996 | Preissman |
| 5,545,168 A | 8/1996 | Burke |
| 5,569,253 A | 10/1996 | Farris et al. |
| 5,609,634 A | 3/1997 | Voydeville |
| 5,611,801 A | 3/1997 | Songer |
| 5,693,072 A | 12/1997 | McIntosh |
| 5,725,582 A | 3/1998 | Bevan et al. |
| 5,766,218 A | 6/1998 | Arnott |
| 5,769,894 A | 6/1998 | Ferragamo |
| 5,788,697 A | 8/1998 | Kilpela et al. |
| 5,810,832 A | 9/1998 | Blasingame et al. |

(List continued on next page.)

OTHER PUBLICATIONS

HOWMEDICA, The DALL–MILES Trochanter Cable Grip System, The Improved Method for Reattachment of the Greater Trochanter, product information sheet, 1990.

HOWMEDICA, The DALL–MILES Cable Grip System, Cerclage Applications Superior Strength and Versatility, product information sheet, 1991.

Primary Examiner—Cary E. O'Connor
Assistant Examiner—Candice C. Melson
(74) Attorney, Agent, or Firm—Lerner, David, Littenberg, Krumholz & Mentlik, LLP

(57) ABSTRACT

A novel system and method for use for ensuring appropriate positioning of a cable about bone portions, particularly, vertebral bone, for stabilization of the spine during spinal reconstructive and fusion procedures is disclosed. The system includes cabling uniquely adapted for spinal reconstruction processes, ligature passers and hook passers of varying sizes to facilitate looping of the cable about the spinal/vertebral bone, and a tensioning apparatus which secures the cable at a predetermined tensioned value about the vertebral bone. A novel method for applying a cable about vertebral bone for spinal stabilization is also disclosed.

6 Claims, 13 Drawing Sheets

U.S. PATENT DOCUMENTS

| | | |
|---|---|---|
| 5,885,291 A | 3/1999 | Moskovitz et al. |
| 5,885,292 A | 3/1999 | Moskovitz et al. |
| 5,902,305 A | 5/1999 | Beger et al. |
| 5,908,421 A | 6/1999 | Beger |
| 5,913,875 A | 6/1999 | Smith et al. |
| 5,919,199 A | 7/1999 | Mers Kelly et al. |
| 5,935,130 A | 8/1999 | Kilpela et al. |
| 5,935,133 A | 8/1999 | Wagner et al. |
| 5,964,765 A | 10/1999 | Fenton, Jr. et al. |
| 5,964,769 A | 10/1999 | Wagner et al. |
| 5,989,256 A | 11/1999 | Kuslich et al. |
| 5,997,542 A | 12/1999 | Burke |
| 6,080,157 A | 6/2000 | Cathro et al. |
| 6,146,386 A | * 11/2000 | Blackman et al. .......... 606/103 |

* cited by examiner

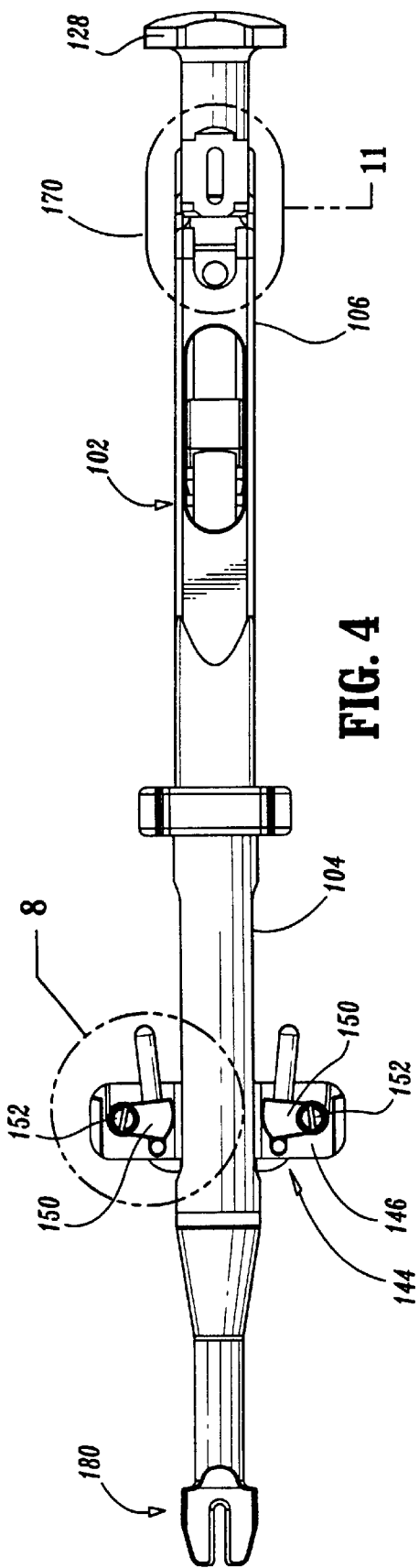
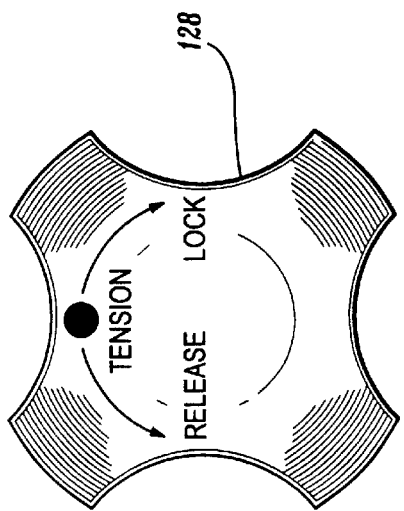
FIG. 4
FIG. 5

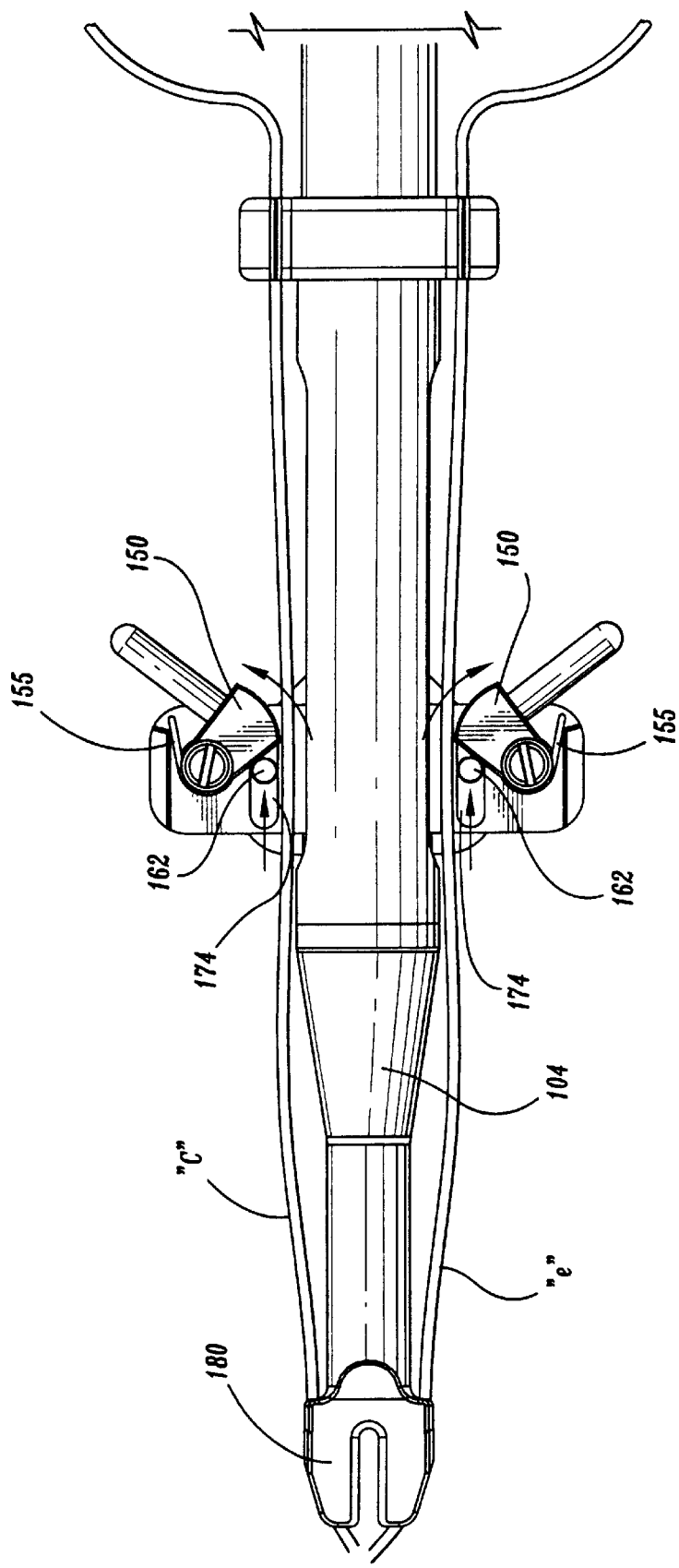

SYSTEM AND METHOD FOR SPINAL RECONSTRUCTION

CROSS-REFERENCE TO RELATED APPLICATIONS

This application claims the benefit of U.S. Provisional Patent Application No. 60/237,169, filed Oct. 2, 2000, the entire disclosure of which is hereby incorporated by reference.

BACKGROUND

1. Field of the Disclosure

The present invention is directed to orthopaedic reconstruction, and more particularly, to a system and method for spinal reconstruction and stabilization of the cervical, lumbar and thoracic spine.

2. Discussion of the Prior Art

Surgical apparatii intended for reconstructive spine surgery and reconstructive spinal procedures in conjunction with bone fusion are known. These apparatii may typically include metal cables and wires which are looped to encircle adjacent bones to hold them together for healing or fusion. The wires may be clamped together to ensure the cable is retained in a looped tensioned condition about the bone portions. Tensioning apparatii are often used to apply a predetermined tension to the cable.

Known cable systems are subject to several disadvantages which detract from their usefulness in spinal reconstruction surgery. In particular, there are significant complications with the use of metal wires and cables, including breakage of the wire and cable, difficulty in maneuvering about the operative site, cutting into the bone and interference with imaging procedures. The known tensioning apparatii are complicated and difficult to manipulate. Moreover, known systems fail to adequately facilitate the cable looping and securing process, and are deficient in securing a bone graft utilized in the fusion/healing process.

SUMMARY OF THE INVENTION

Accordingly, the present invention is directed to a novel system and method for use for ensuring appropriate positioning of a cable about bone portions, particularly, vertebral bone, for stabilization of the spine during spinal reconstructive and fusion procedures. The system includes cabling uniquely adapted for spinal reconstruction processes, ligature passers and hook passers of varying sizes to facilitate looping of the cable about the spinal/vertebral bone, and a tensioning apparatus which secures the cable at a predetermined tensioned value about the vertebral bone. A novel method for applying a cable about vertebral bone for spinal stabilization is also disclosed.

BRIEF DESCRIPTION OF THE DRAWINGS

Preferred embodiments of the disclosure are described in further detail herein with reference to the drawings wherein:

FIG. 4 is a top plan view of the apparatus of FIG. 1;

FIG. 5 is an axial plan view of the control knob of the apparatus illustrating the knob's operating positions;

FIGS. 9 and 10 are top plan views of the tensioning apparatus illustrating the cable engaging pawls in an engaged position and disengaged position, respectively;

DETAILED DESCRIPTION OF PREFERRED EMBODIMENTS

Figure 1:
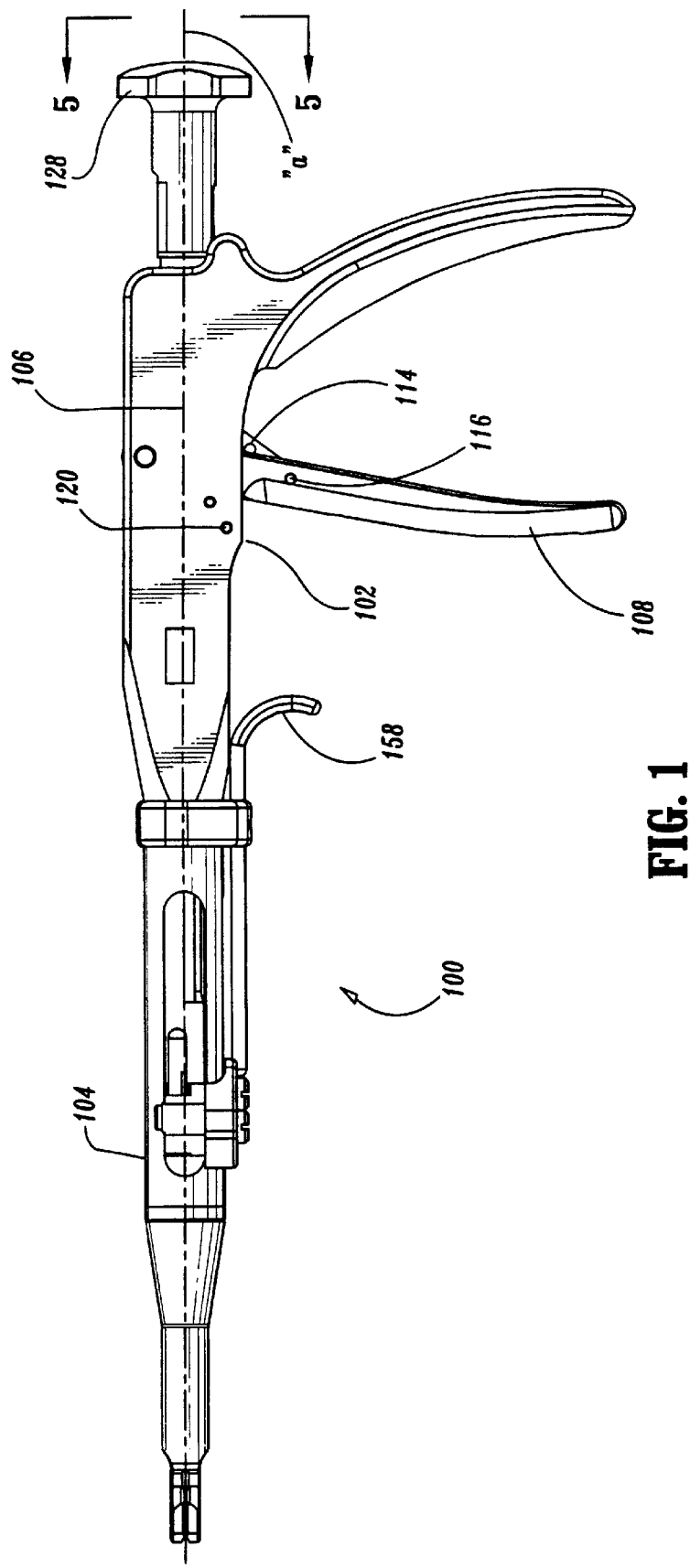
FIG. 1 is a side plan view of the tensioning apparatus of the system for orthopaedic spinal stabilization in accordance with the principles of the present disclosure.

Referring now to the drawings wherein like references identify similar or like elements throughout the several views, there is illustrated the system for spinal stabilization in accordance with the principles of the present disclosure.

The following discussion will include a description of each instrument utilized in performing a spinal procedure followed by a description of preferred methods for spinal stabilization utilizing the instrumentation in accordance with the present disclosure.

In the discussion which follows, the term "proximal", as is traditional, will refer to the portion of the structure which is closest to the operator, while the term "distal" will refer to the portion which is furthest from the operator.

The system for spinal stabilization includes several components, namely, a surgical cable, a tensioning apparatus for applying the surgical cable about the spinal bone, and hook and ligature passers utilized to facilitate looping of the cable about the bone. The preferred surgical strand or cable is a radiolucent cable system known under the trademark SecureStrand™ which is available from Surgical Dynamics, Inc. of Norwalk, Conn. This cable is made of braided high strength radiolucent ultra-high molecular weight polyethylene (UHMWPE) fiber. The cable consists of 8 yarns of fiber, each having 120 fibers, and being braided to form a cable about 1 mm in diameter. The cable derives its strength from the unique fibers used to create it. These extended-chain polyethylene fibers are characterized by a high degree of orientation with a minimum of chain folding. The SecureStrand™ cable system avoids many of the potential complications caused by implantation of metal wires and metal cables, including wire/cable breakage, hemorrhage, contusion, laceration and interference with magnetic resonance and x-ray imagery. Furthermore, the cable is sufficiently flexible for looping about bone tissue and may be secured relative to bone tissue through knotting procedures.

Figure 2:
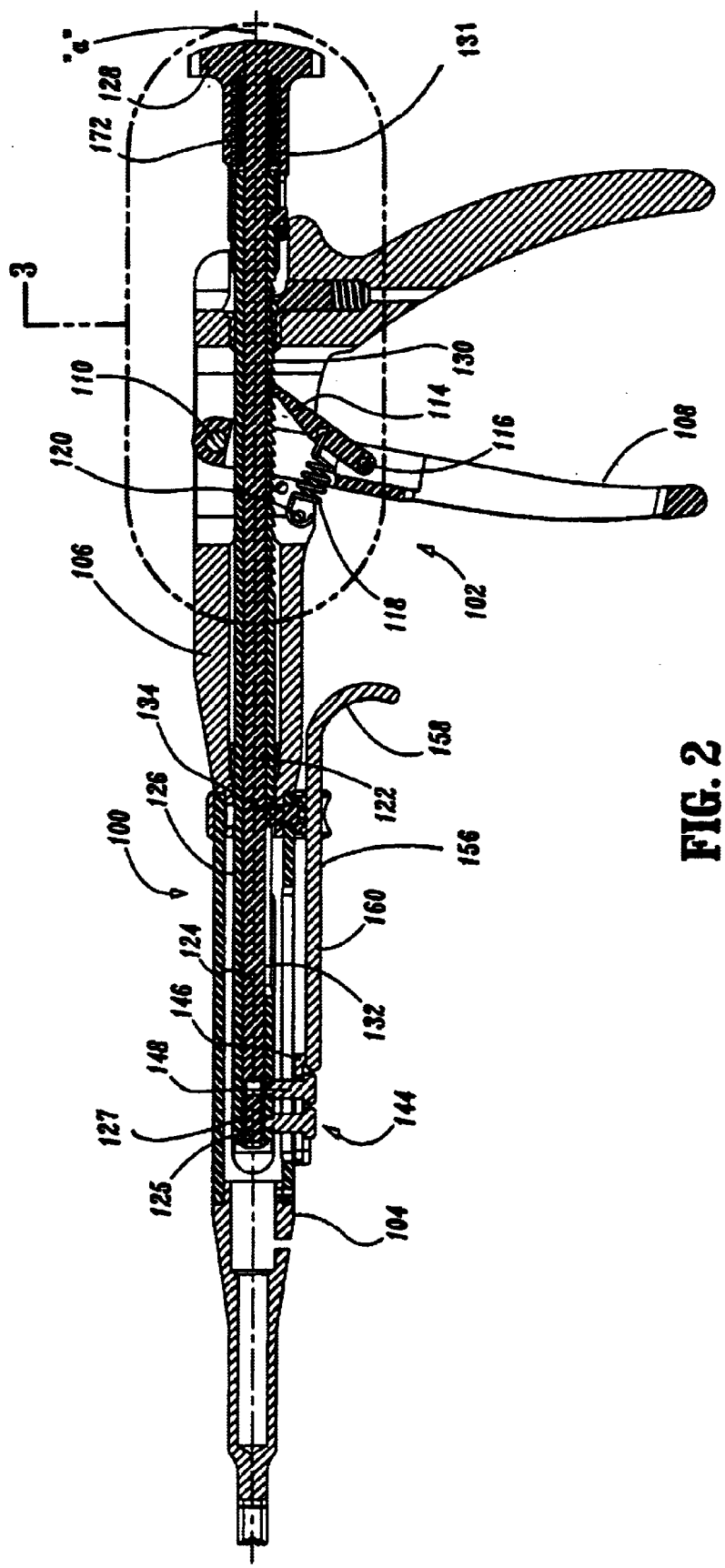
FIG. 2 is a side cross-sectional view of the tensioning apparatus of FIG. 1.

Referring now to FIG. 1, in conjunction with FIGS. 2–4, tensioner apparatus of the system will be discussed. Tensioning apparatus 100 includes a handle 102 and an elongated member 104 extending distally from the handle 102, and defining a longitudinal axis "a". Handle 102 includes frame 106 having a stationary grip and a movable grip 108 pivotally mounted within the frame 106 about pivot pin 110. Movable grip 108 includes pawl 114 which forms part of the ratchet mechanism for tensioning the cable. Pawl 114 pivots about pivot pin 116 and has a coil spring 118 which biases the pawl 114 distally to a normally engaged position corresponding to an operative position of the ratchet mechanism as depicted in FIG. 2. Coil spring 118 is connected to handle 102 through pin 120.

An elongated actuating member 122 extends through frame 106 and elongate member 104. Actuating member 122 includes an inner rod 124 and an outer sleeve 126 coaxially mounted about the rod 124. A screw 125 received within a corresponding threaded aperture 127 at the distal end of rod 124 engages the distal end of outer sleeve 126 such that the inner rod 124 and outer sleeve 126 move concurrently in the distal direction. Outer sleeve 126 is adapted for rotational movement relative to rod 124 and has control knob 128 coaxially mounted to its proximal end through stationary screw 131. Outer sleeve 126 includes ratchet teeth 130 which cooperate with pawl 114 of movable grip 108 to move outer sleeve 126. Outer sleeve 126 further defines a longitudinal slot 132 within the elongate member 104 in which an internal sleeve locking pin 134 is received (FIG. 2).

Figure 6A:
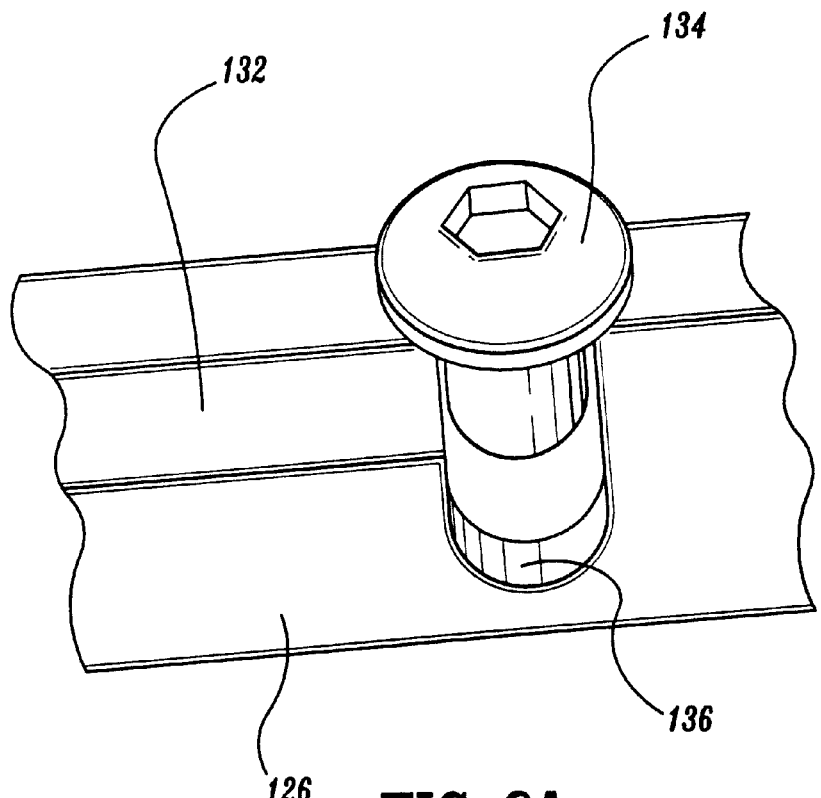
FIGS. 6A and 6B are schematic views illustrating release and locking positions of the apparatus.
Figure 6B:
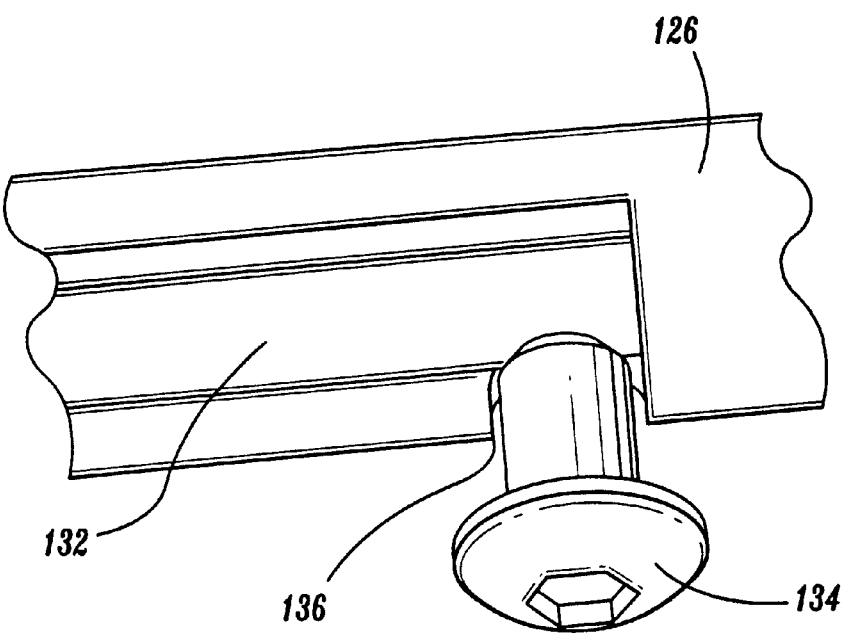
Figure 7:
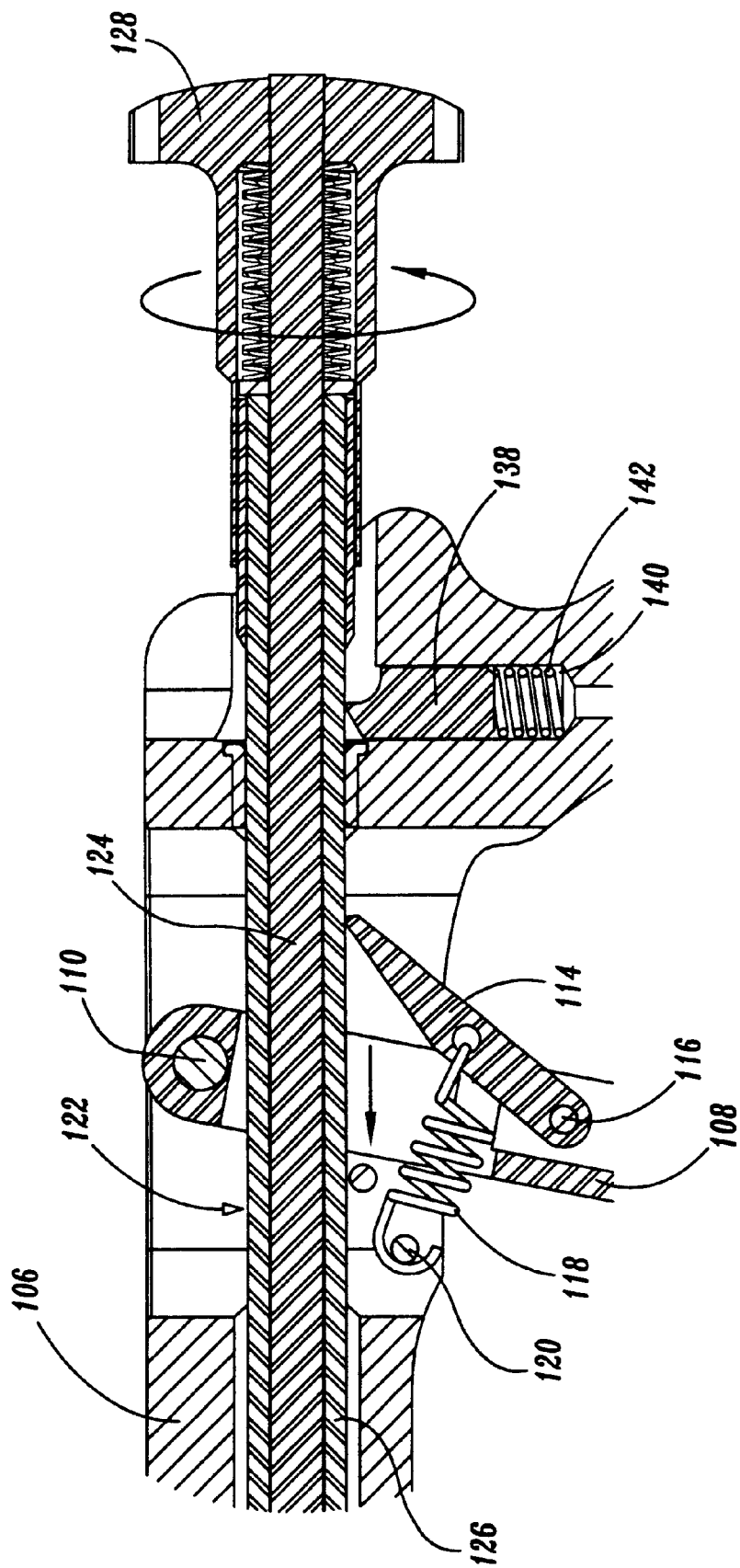
FIG. 7 is a view similar to the view of FIG. 3, illustrating rotation of the control knob corresponding to a release position of the apparatus.

As best depicted in FIG. 5, locking knob 128 is rotatable about the longitudinal axis "a" through at least three positions, namely, "release", "tension" and "lock" positions, to cause rotational movement of the outer sleeve 126 through three corresponding positions. In the "tension" position, which is depicted in FIG. 2, ratchet teeth 130 of outer sleeve 126 are engaged with pawl 114, thereby permitting the outer sleeve 126 to move upon movement of movable grip 108 to tension the cable. Also in the "tension" position, sleeve locking pin 134 is disposed in longitudinal slot 132 of the outer sleeve 126 such that the locking pin 134 traverses the longitudinal slot 132 during axial movement of outer sleeve. This relationship is shown schematically in FIG. 6A. In the "release" position depicted in the cross-sectional view of FIG. 7, control knob 128 is rotated in a counter-clockwise direction (FIG. 5) to rotate outer sleeve 126, i.e., outer sleeve 126 is angularly displaced whereby ratchet teeth 130 are disengaged from pawl 114 thereby permitting actuating member 122 to move without restriction in either the proximal direction or distal direction. In the "lock" position, control knob 128 is rotated clockwise with respect to FIG. 5, "¼" turn through an angular displacement of 90°. In this position, internal locking pin 134 is received within a transverse groove 136 extending from longitudinal slot 132 of outer sleeve 126 thereby preventing the outer sleeve 126 from moving axially as depicted in the schematic view of FIG. 6B. Thus, in the "lock" position, the instrument is not capable of being used in a tensioning mode of operation.

With reference again to FIGS. 2 and 3, the pawl mechanism further includes a ratchet lock 138 disposed within frame 106 of handle 102 adjacent control knob 128. Ratchet lock 138 moves transversely relative to the longitudinal axis "a" within slot 140 of frame 106 to releasably engage/disengage ratchet teeth 130 of actuating member 122. Ratchet lock 138 is biased to the engaged position depicted in FIG. 3 by coil spring 142. Ratchet lock 138 is adapted to releasably lock outer sleeve 126 of actuating member 122 subsequent to each incremental movement of the outer sleeve 126 in a proximal or tensioning direction, i.e., the ratchet lock 138 is displaced downwardly upon engagement of pawl 114 with a crest 130c of each respective ratchet tooth whereby upon clearance of the crest 130c the ratchet lock 138 engages the leading vertical surface 130v of the tooth. Accordingly, when in the "tension" condition of control knob 128 the pawl mechanism releasably incrementally locks outer sleeve 126 actuating member 122 while preventing distal loosening movement thereof. Ratchet lock 138 also provides an audible signal during each "click" of the ratchet teeth to indicate the progression of the tensioning procedure.

Figure 8:
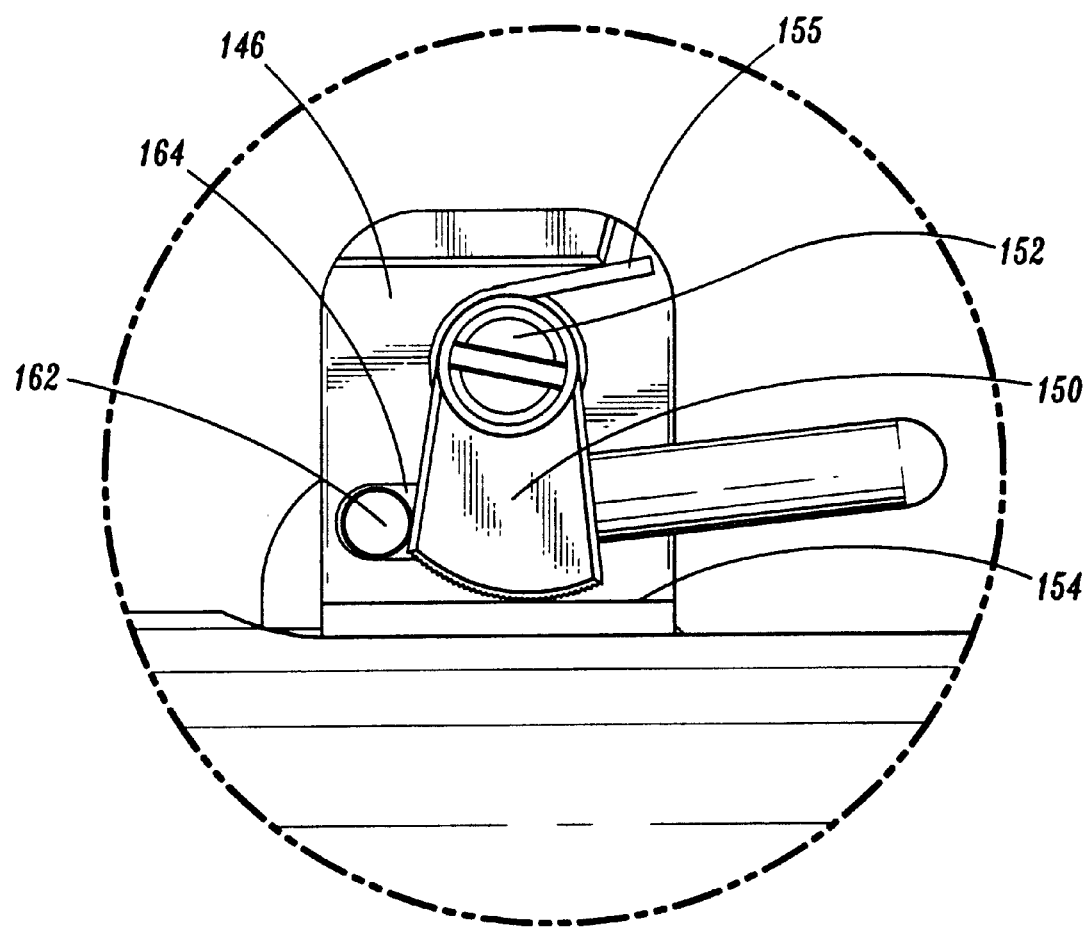
FIG. 8 is an isolated view of a cable engaging pawl of the tensioning apparatus.

With reference to FIGS. 2, 4 and 8, apparatus 100 further includes a cable engaging pawl mechanism 144 adjacent its distal end. Cable engaging pawl mechanism 144 includes plate 146 which is operatively connected to outer sleeve 126 of actuating member 122 through screw 148. Plate 146 moves longitudinally upon longitudinal movement of outer sleeve 126. A pair of cable engaging pawls 150 are pivotally mounted to plate 146 through pivot screws 152 on opposed sides of elongated member 104. Each cable engaging pawl 150 is movable about screw 152 between a cable engaging position depicted in FIGS. 4, 8 and 9 and a cable release position. In the engaging position depicted in FIG. 9, the pawls 150 clamp the cable ends "e" against respective vertical surfaces 154 of plate 146. Each pawl 150 is normally biased to the engaged position through torsional spring 155 which is coaxially mounted about each screw 152.

A cable release trigger 156 extending beneath elongate member 104 moves the pair of cable engaging pawls 150 between the cable engaging and release positions. More particularly, release trigger 156 includes a U-shaped portion 158 engageable by the index finger of the user and release rod 160 which extends to plate 146. Release rod 160 is operatively connected to a pair of cam pins 162 which are received within corresponding slots 164 of plate 146. Each cam pin 162 traverses its respective slot 164 upon longitudinal movement of release trigger 156 to open and close cable engaging pawls 150. In particular, upon depressing or proximal movement of release trigger 156, the cam pins 162 connected to the release rod 160 move proximally within slots 164 to engage pawl 150 to open the pawls 150 to the position depicted in FIG. 10. Release of release trigger 156 permits pawls 150 to return to their normal engaged position under the influence of torsion springs 155.

Figure 3:
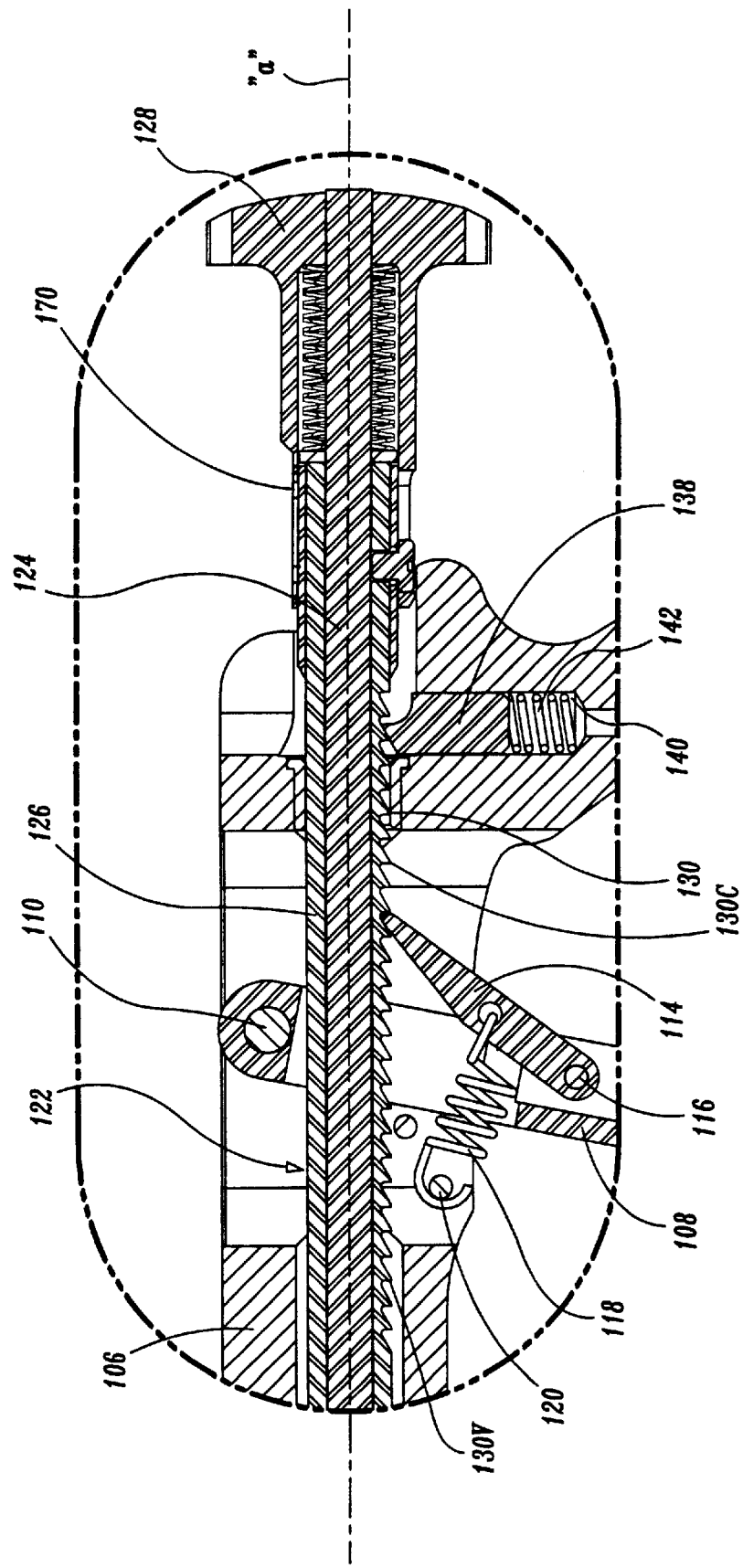
FIG. 3 is an enlarged isolated view of the ratcheting mechanism of the tensioning apparatus.
Figure 11:
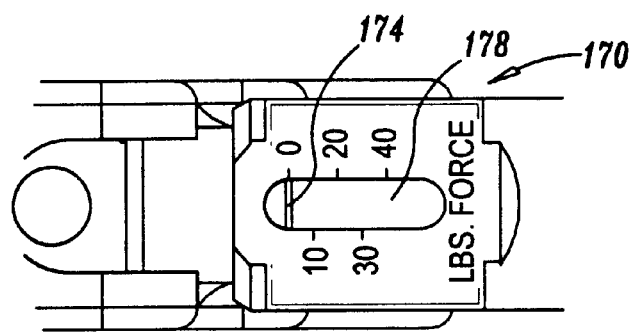
FIG. 11 is an isolated view of the graduated scale mechanism indicating the degree of tension of the looped cable.

With reference now to FIGS. 3, 4 and 11, tensioner apparatus 100 further includes a graduated spring scale 170 disposed adjacent control knob 128 to indicate to the user the degree of tension of the cable. Spring scale 170 includes spring 172 and an indicator pin 174 which is operatively connected to the pin 172. Pin 172 extends through slot 176 of indicator panel 178. Spring 172 operatively engages the proximal end of outer sleeve 126 of actuating member 122. When the outer sleeve 122 is displaced rearwardly upon movement of tensioning trigger 108, spring 172 is compressed accordingly. The degree of compression of spring 172 which is directly related to the forces on actuating member 122 through the tensioned cable is indicated by the location of scale pin 174 relative to the graduated markings on the indicator panel 178. This permits the surgeon to readily obtain the level of tension of the cable.

Figure 9:
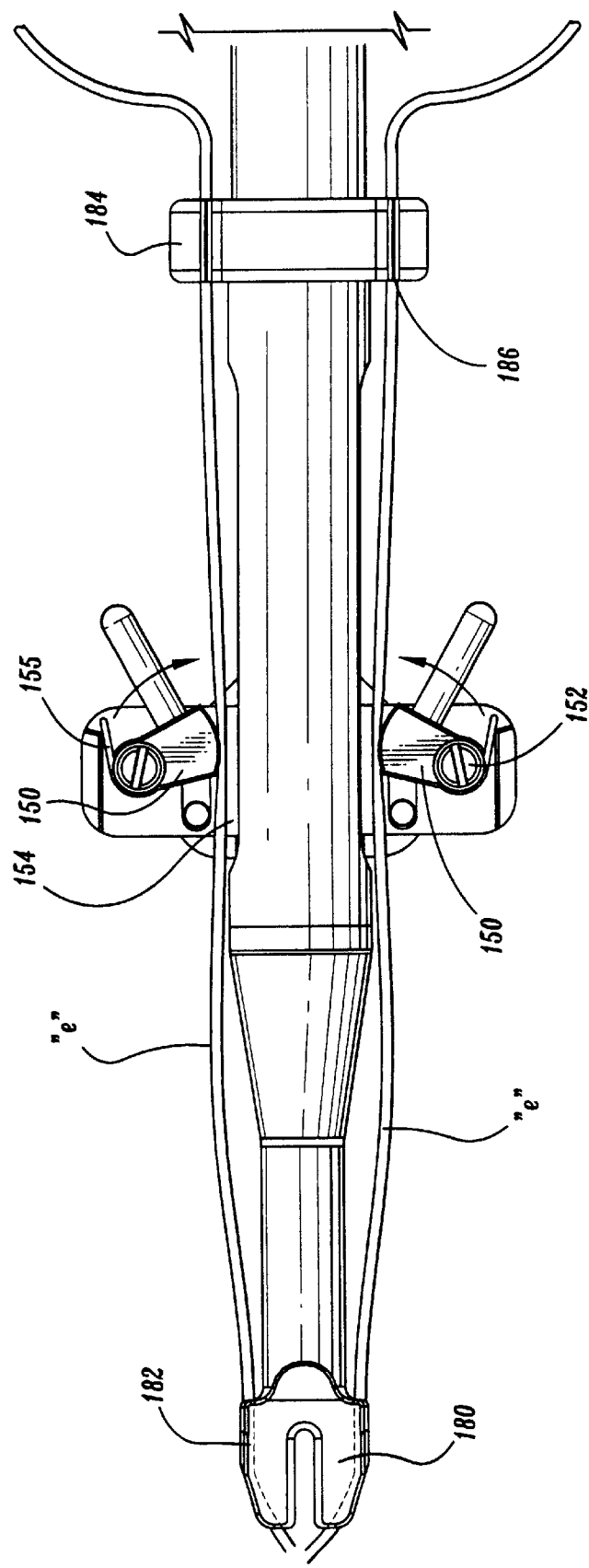

Referring now to FIG. 9, in conjunction with FIG. 1, tensioning apparatus 100 further includes a distal bull nose 180. Bullnose 180 includes opposed cable receiving grooves 182 (phantom) which receive each cable end "e" prior to passing through the cable pawl mechanism 144. Apparatus 100 also includes a plastic collar 184 having grooves 186 which receives the extreme free ends of the cable "c".

Figure 12:
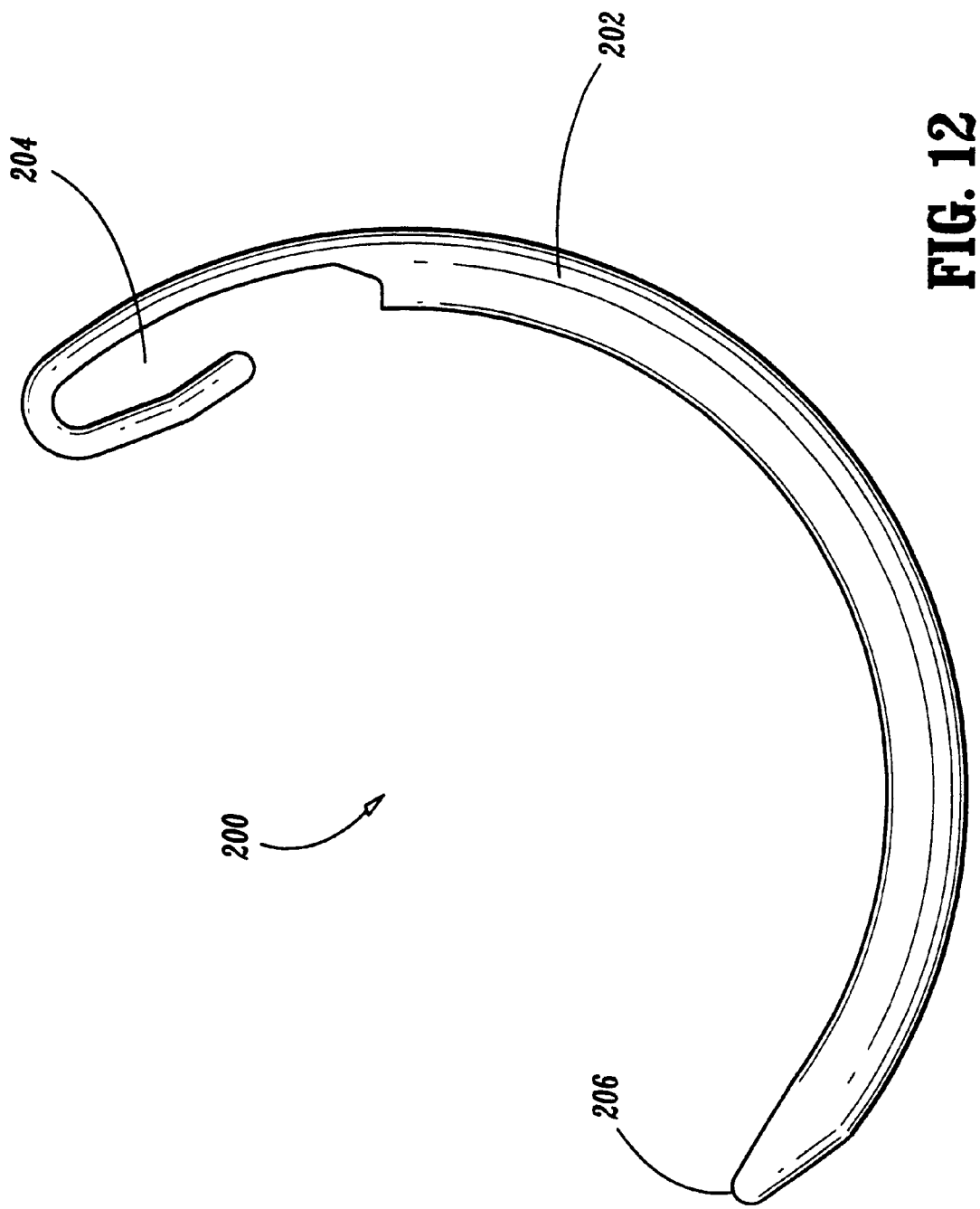
FIG. 12 is a side plan view of the hook passer of the system.

Referring now to FIG. 12, hook passer 200 of the system will be discussed. Hook passer 200 is intended to pass the SecureStrand™ cable about adjacent vertebral bodies. Hook passer 200 includes a hook body 202 defining a general semi-circular shape and having an eye loop 204 at a trailing end and a narrowed blunt entry end 206. Eye loop 204 is generally elongated and is dimensioned for reception of the looped cable end. During manufacture, eye loop 204 is bent in itself to define an open hook appearance detailed in the Figure.

Figure 13A:
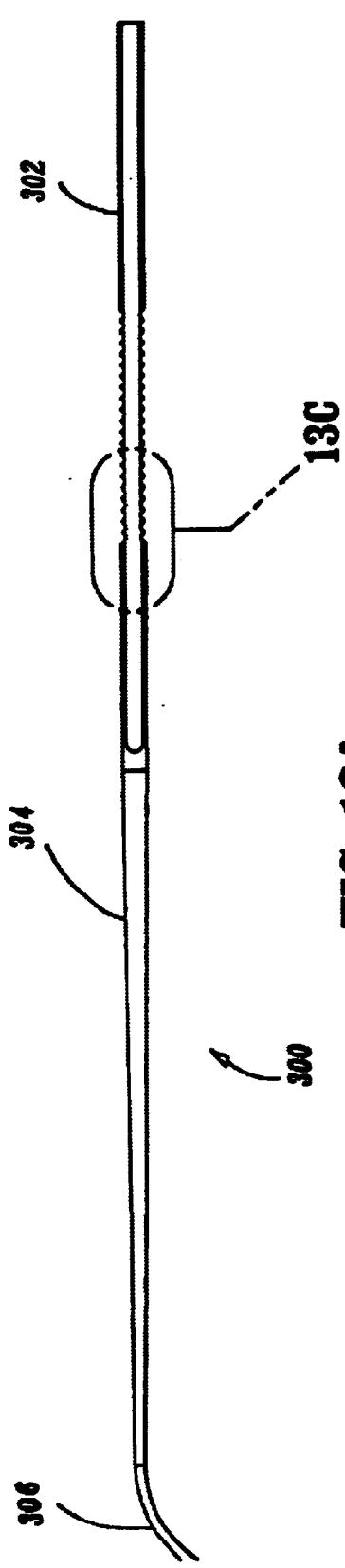
FIGS. 13A–13C are views of the ligature passer of the system.
Figure 13C:
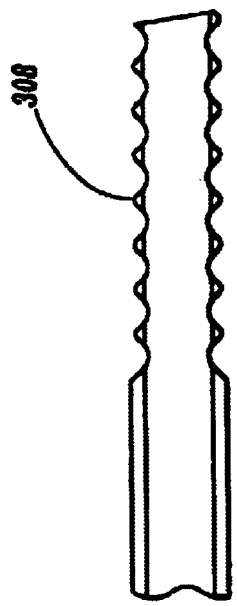
Figure 13B:
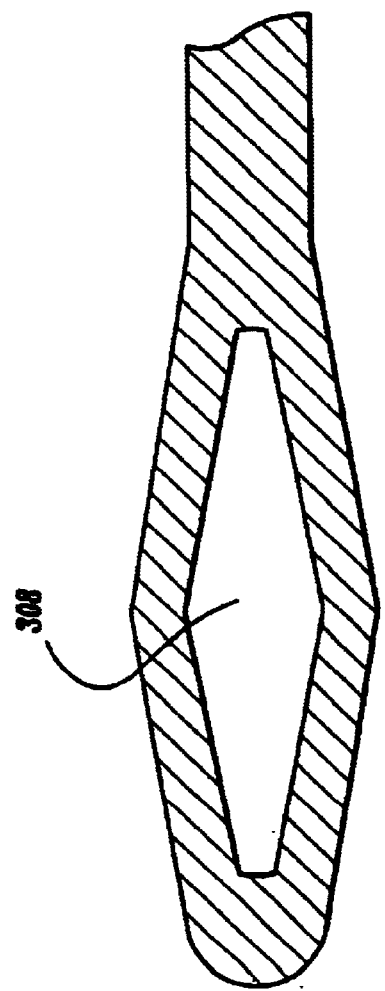

With reference now to FIGS. 13A–C, ligature passer 300 of the system will be discussed. Ligature passer 300 is also intended for looping the cable end with respect to the vertical bodies and includes handle 302 and elongated portion 304 extending distally from the handle 302. Elongated portion 304 includes an arcuate end portion 306 which is bent between an angle ranging about 70°–110° relative to the axis "a" of the elongated portion. The extreme distal end of the ligature passer includes an eye loop 308 dimensioned for reception of the looped SecureStrand™ cable. The handle 302 includes a knurled portion 308 to facilitate gripping engagement by the user.

Figure 14:
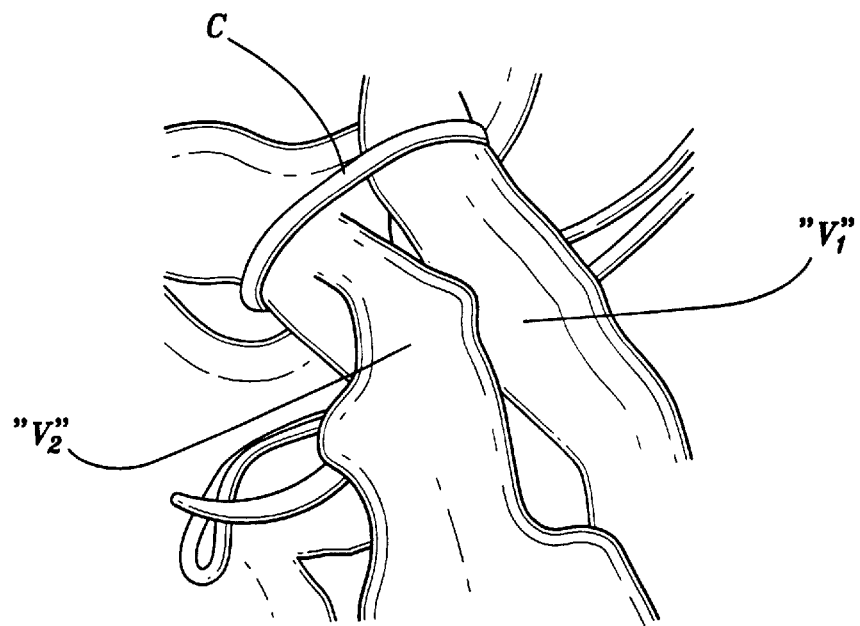
FIGS. 14–17 are views illustrating the sequence of use of the instruments of the system in accordance with a preferred procedure for spinal stabilization.

The use of system 100 for spinal stabilization will now be discussed. Subsequent to removal of a portion of the vertebrae and/or removal of an intervertebral disc, the spine is to be stabilized for healing and fusion. A three foot length of SecureStrand™ cable is cut from a cable roll and folded upon itself. With the assistance of hook passer 200 or ligature passer 300, depending on the preference of the surgeon, the looped end of the cable "c" may be engaged to respective eye loops of the passers, and the passers are manipulated to pass the cable "c" beneath a pair of opposed vertebrae $V_1$, $V_2$, i.e., the spinous process or adjacent lamina as depicted in FIG. 14.

Figure 15:
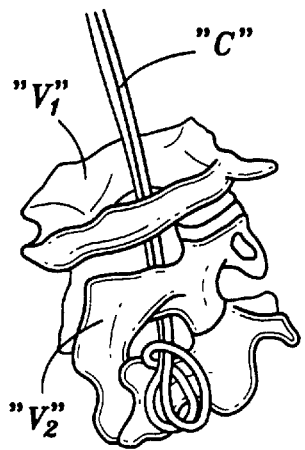
Figure 16:
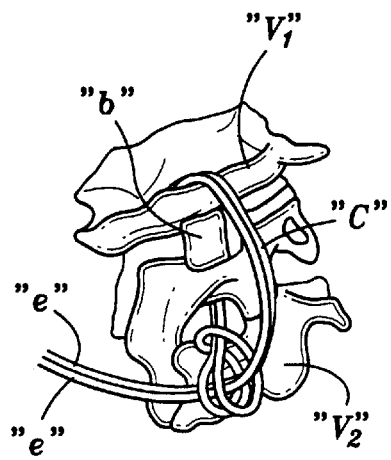
Figure 17:
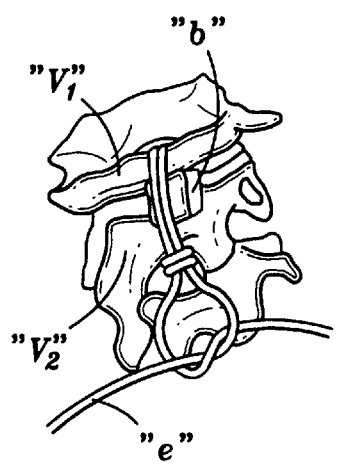

Once the looped cable "c" is positioned with respect to the vertebral bone portions $V_1$, $V_2$, attention is directed to tying the appropriate knot with the cable "c". In the preferred procedure, a racking hitch is formed in the looped cable end by inwardly twisting the cable loop upon itself to the orientation depicted in FIG. 15. In procedures involving fusion, a bone graft "b" may be placed between the vertebrae. Thereafter, both free ends "e" of the cable "c" are pulled through the racking hitch as depicted in FIG. 16. The bone graft "b" is shown in FIG. 16. Both free ends are advanced in order to close the racking hitch against the vertebral bodies $V_1$, $V_2$. Thereafter, the free ends of the cable "c" are used to tie a half hitch, as depicted in FIG. 17. The half hitch is advanced to abut the racking hitch to secure the bone graft between the adjacent vertebrae $V_1$, $V_2$. The half hitch is tightened with moderate hand pressure.

Figure 19:
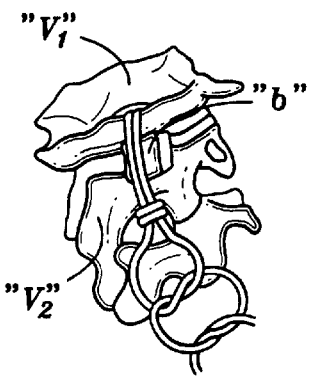
FIG. 19 is a view illustrating securement of the looped cable.
Figure 18:
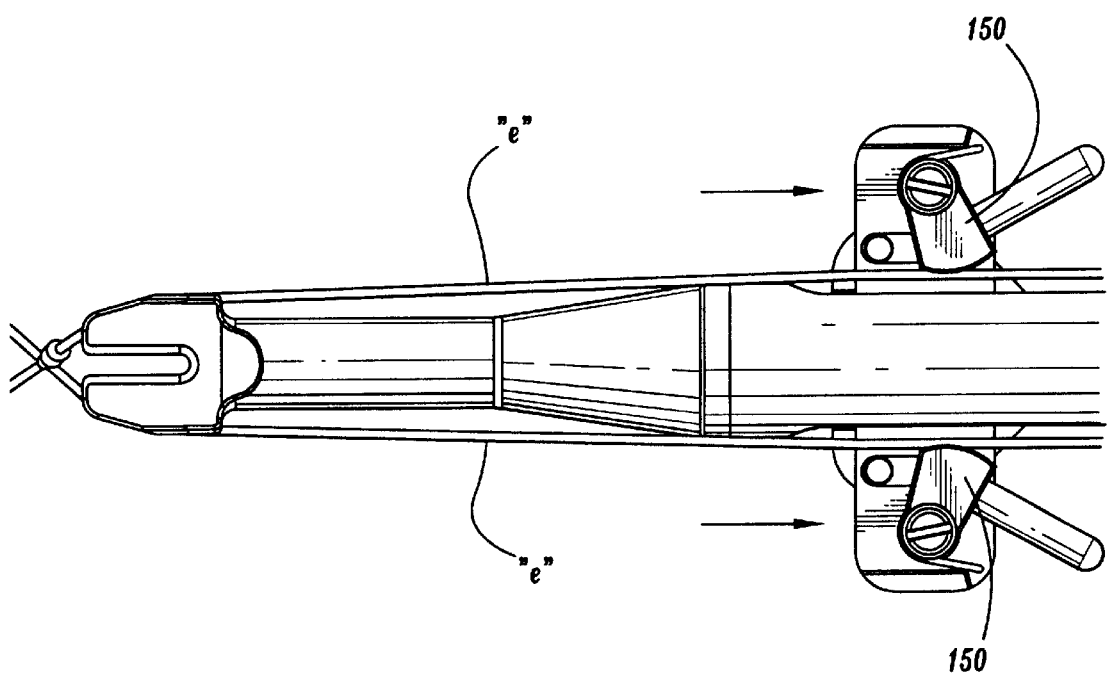
FIG. 18 is a top plan view illustrating movement of the pawl engaging mechanism during actuation of the movable grip.

The procedure is continued by applying tension to each of the cable ends. Tensioner apparatus 100 is introduced into the surgical site. A first free end "e" of the cable "c" is positioned about the bull nose 180 of the apparatus with the cable receiving groove 182 and the second free end "e" is positioned within the opposed groove 182 as depicted in FIG. 9. With reference to the FIG. 10, the cable release trigger is depressed to outwardly displace the cable engaging pawls 150 to permit the cable ends "e" to be passed within the openings defined between the pawls 150 and the vertical surfaces 154 of plate 146. Thereafter, the extreme ends of the cable "c" are positioned within grooves 186 of holder 184 as also depicted in FIG. 10. Movable grip 108 is actuated to move, through action of the ratchet mechanism, actuating member 122, plate 146 and cable engaging pawls 150 proximally as depicted in FIG. 18 to tighten the cable ends. During actuation, spring scale 170 is continually monitored to monitor the desired degree of tension to the cable strands. Once the desired level of tension is achieved, control knob 128 is rotated to the "release" position, and the control knob is pushed forwardly. Then, the control knob is rotated to the "lock" position. The cable release trigger is depressed to release the cable from the pawls and the ends of the cable are removed from the plastic holder. As depicted in FIG. 19, a second half hitch opposite to the first half hitch is created to form a square knot. A third half hitch is then formed opposite the second half hitch and advanced to the square knot to secure the cable. Thereafter, the free ends of the cable are cut beyond the knob with, e.g., a cauterizer.

While the above description contains many specifics, these specifics should not be construed as limitations on the scope of the disclosure, but merely as exemplifications of preferred embodiments thereof. Those skilled in the art will envision other modifications within the scope and spirit of the claims appended hereto. For example, the system and method of application can be utilized in other areas of the body including knee, hip elbow etc . . . to join adjacent bone portions.

What is claimed is:

1. A tensioning apparatus for applying a predetermined level of tension to a cable looped about tissue portions, which comprises:
    a handle;
    an elongated member extending from the handle and defining a longitudinal axis;
    first and second cable engaging pawls mounted to the elongated member for releasably engaging respective ends of the cable;
    a movable grip mounted to the handle; and
    an actuating member connected to the movable grip and adapted to longitudinally translate upon movement of the movable grip, the actuating member operatively connected to the cable engaging pawls whereby movement of the movable grip causes corresponding movement of the cable engaging pawls to tension the cable.

2. The tensioning apparatus according to claim 1 further including a manually engageable release member, the release member movable to move the cable engaging pawls to a disengaged position with respect to the cable ends.

3. The tensioning apparatus according to claim 2, wherein the cable engaging pawls are normally biased to an engaged position with respect to the cable ends.

4. The tensioning apparatus according to claim 3, including a ratchet and pawl associated with the movable grip and actuating member for providing incremental movements of the actuating member.

5. The tensioning apparatus according to claim 4, including a control knob for controlling operation, the control knob being movable between three positions corresponding to lock, tension and release positions, wherein in the lock position, the actuating member is prevented from axially moving in a tensioning direction, wherein in the tension position, the ratchet and pawl are engaged with the actuating member to permit axial movement of the actuating member in the tensioning direction, and wherein, in the release position, the ratchet and pawl are disengaged thereby permitting unrestricted movement of the actuating movement in the tensioning direction and a release direction.

6. The tensioning apparatus according to claim 5, including a second pawl engageable with the ratchet to prevent movement of the actuating member in the release direction.

* * * * *

UNITED STATES PATENT AND TRADEMARK OFFICE
CERTIFICATE OF CORRECTION

PATENT NO. : 6,689,140 B2
DATED : February 10, 2004
INVENTOR(S) : Herb Cohen

It is certified that error appears in the above-identified patent and that said Letters Patent is hereby corrected as shown below:

<u>Drawings,</u>
Sheet 9, FIG. 10, first and second occurrence of "174" should read -- 164 --.

<u>Column 4,</u>
Line 50, first occurrence of "pin" should read -- spring --.
Line 50, second occurrence of "172" should read -- 174 --.

Signed and Sealed this

Fifteenth Day of June, 2004

JON W. DUDAS
*Acting Director of the United States Patent and Trademark Office*